United States Patent [19]
Tsuboi

[11] Patent Number: 5,144,838
[45] Date of Patent: Sep. 8, 1992

[54] DEFECT DETECTING METHOD AND APPARATUS

[75] Inventor: Kiyoshi Tsuboi, Tokyo, Japan

[73] Assignees: Iwatsu Electric Co., Ltd.; Honda Giken Kogyo Kabushiki Kaisha, both of Tokyo, Japan

[21] Appl. No.: 711,908

[22] Filed: Jun. 7, 1991

Related U.S. Application Data
[62] Division of Ser. No. 592,247, Oct. 3, 1990.

[30] Foreign Application Priority Data

Oct. 4, 1989 [JP] Japan .................. 1-259183

[51] Int. Cl.⁵ .......................................... G01N 29/12
[52] U.S. Cl. .................................. 73/579; 364/508; 73/646
[58] Field of Search ............... 73/579, 582, 583, 602, 73/592, 645, 646, 658, 659; 364/508

[56] References Cited

U.S. PATENT DOCUMENTS

| | | | |
|---|---|---|---|
| 3,106,838 | 10/1963 | Crooks | 73/582 |
| 3,345,861 | 10/1967 | Heath | 73/579 |
| 3,623,358 | 11/1971 | Sugimoto | 73/579 |
| 3,659,456 | 5/1972 | Marshall et al. | 73/659 |
| 3,842,663 | 10/1974 | Harting et al. | 73/659 |
| 3,916,699 | 11/1975 | Moran et al. | 73/592 |
| 4,114,454 | 9/1978 | Ernyei et al. | 73/579 |
| 4,408,294 | 10/1983 | Imam | 364/508 |

FOREIGN PATENT DOCUMENTS

| | | | |
|---|---|---|---|
| 0151725 | 7/1987 | Japan | 73/659 |
| 0293151 | 12/1987 | Japan | 73/579 |

*Primary Examiner*—Hezron E. Williams
*Assistant Examiner*—Rose M. Finley
*Attorney, Agent, or Firm*—Oblon, Spivak, McClelland, & Maier Neustadt

[57] ABSTRACT

A defect detecting method for detecting whether or not an object to be measured has a defect comprises the steps of vibrating the object to be measured, picking up the vibration, and detecting that a spectrum of the characteristic vibration of the object to be measured is separated into two portions. Also, a defect detecting apparatus comprises a vibrator vibrating an object to be measured, a detector for picking up an vibration of the object to be measured and for converting the vibration into an electric signal, and a signal processor for receiving the electric signal from the detector, for analyzing a spectrum of a characteristic vibration of the object to be measured, and for determining whether the defect is present or absent depending on whether a spectrum of a defect of the object to be measured is present or absent.

9 Claims, 8 Drawing Sheets

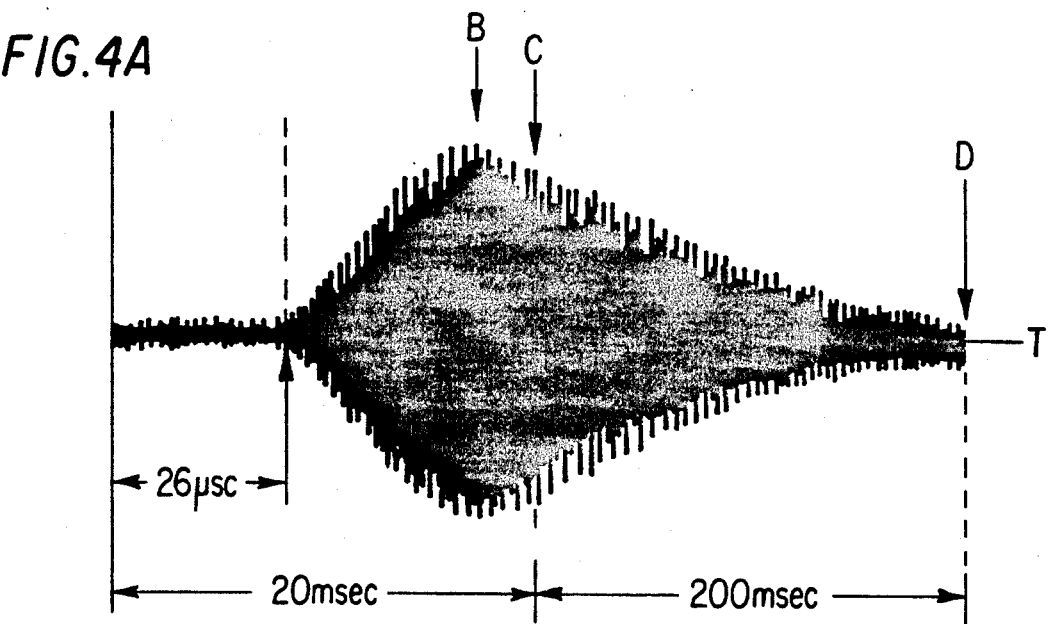
FIG.4A
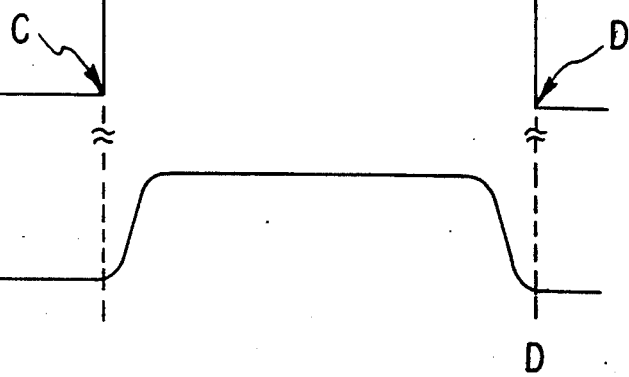
FIG.4B (W₁)
FIG.4C (W₂)

and apparatus

This is a division of application Ser. No. 07/592,247, filed on Oct. 3, 1990.

BACKGROUND OF THE INVENTION

1. Field of the Invention

The present invention relates to a defect detecting method and apparatus for detecting a defect such as a crack, a void, or a dent which is present in an object to be measured.

2. Description of the Related Art

For example, if the cylinder part or the piston part used in an automobile engine has a defect such as a crack, void, or dent, the cylinder mechanism or the piston mechanism gets defective. To prevent that, it is preferable to detect the part which has the crack, void, or dent in the production line thereof before assembling the automobile engine.

Conventionally, as such defect detecting methods, ultrasonic reflection method, AE (acoustic emission) crack sound detecting method, CCD camera observation method, X ray photographing method, color check method, eddy current method, and so forth have been known.

However, the aforementioned methods have the following problems in handling thereof.

For example, in the ultrasonic reflection method (ultrasonic flaw detecting method), a sensor brings in contact with an object to be measured to detect a defect. Thus, only a defect with which the sensor brings in contact can be detected due to the property of rectilinear propagation of ultrasonic waves. In addition, the wave forms observed vary with reflection due to irregular connecting surface of the sensor and with an angular difference. Thus, this method involves a difficulty for determining the defect.

In the case of the AE method, like the ultrasonic flow detecting method, a sensor brings in contact with an object to be measured. In addition, in this method, only a progressive crack is detectable. Conversely, when the progressive crack is measured, it becomes large.

In the CCD camera observation method, besides a crack and a dent, a stain and a pattern also disadvantageously affect the determination result of the measurement. In addition, in this method, a void called a "cavity" in a casting cannot be determined.

In the X ray photographing method, a defect can be directly observed. However, the adjustment of the X ray amount is difficult and accordingly, the 100% inspection of the objects to be measured cannot be conducted. Thus, this method cannot be used on the production line.

In the eddy current method, an object to be measured should be rotated at a high speed. In addition, to an increase in the sensitivity, it is necessary to approach the sensor to the object to be measured and to equally move them. However, if the surface of the object to be measured is uneven, it is very difficult to measure a defect.

SUMMARY OF THE INVENTION

An object of the present invention is to solve the aforementioned problems and to non-contactually and easily detect a defect in an object to be measured.

To achieve the above objects, the present invention provides a defect detecting method for detecting whether or not an object to be measured has a defect, the method comprising the steps of vibrating an object to be measured, picking up the vibration, and detecting that a spectrum of the characteristic vibration of the object to be measured is separated into two portions.

Also, the present invention provides a defect detecting method for detecting a through crack in an object to be measured, the method comprising the steps of vibrating an object to be measured, picking up the vibration, and detecting that an odd order spectrum of the characteristic vibration of the object to be measured is separated into two portions.

Further, the present invention provides a defect detecting method for detecting a non-through defect in the thickness direction of an object to be measured, such as a void or an indentation, the method comprising the steps of vibrating an object to be measured, picking up the vibration, and detecting that an even order spectrum of the characteristic vibration of the object to be measured is separated into two portions.

Further, the invention provides the defect detecting method, wherein a defect of the object to be measured is determined depending on the sharpness of a spectrum of the characteristic vibration of the object to be measured.

Further, the present invention provides a defect detecting method, the method comprises the steps of vibrating an object to be measured, picking up the vibration, converting the picked characteristic vibration of the object to be measured into time series, and detecting whether or not a defect is present according to an envelope of a wave form converted into time series.

Further, the present invention provides a defect detecting apparatus, comprising vibration means for vibrating an object to be measured, pick up means for picking up vibration of the object to be measured and for converting the vibration into an electric signal, and computation process and determination means for receiving the electric signal from the pick up means, for analyzing a spectrum of a characteristic vibration of the object to be measured, and for determining whether the defect is present or absent depending on whether a spectrum of a defect of the object to be measured is present or absent.

Further, the present invention provides a defect detecting apparatus, comprising vibration means for vibrating an object to be measured, pick up means for picking up an vibration of the object to be measured and for converting the vibration into an electric signal, and computation process and determination means for receiving the electric signal from the pick up means, for converting a characteristic vibration of the object to be measured into time series, for obtaining an envelope of the resultant signal, and for determining whether the defect is present or absent depending on the envelope waveform.

According to the method and apparatus of the present invention, an object to be measured is vibrated and then the characteristic vibration intrinsic to the object is non-contactually detected by using a sensor. Thus, as opposed to the sensor contacting method, this method is free from a diffused reflection due to an irregular sensor contact. Thus, the wave form of the vibration can be readily observed. In other words, in measuring a defect in the object to be measured, the factors which disadvantageously affect the measurement are small and thereby the measurement can be stably conducted in a short time because of simple operation and contents for the determination.

In addition, according to the present invention, even if an object to be measured has a wrinkle and/or a dent, when they can be distinguished from the characteristic vibration, a defect, which is, a crack, void such as casting cavity, or dent can be detected.

Moreover, by only vibrating the object to be measured, a defect thereof can be determined entirely not partially.

BRIEF DESCRIPTION OF THE DRAWINGS

FIG. 4A is a waveform of the vibration of an object to be measured just after it is vibrated;

FIG. 4B is a rectangular waveform window, W1 for emphasizing a portion of a vibration wave form;

Fig 4C is a waveform window W2 for emphasizing a portion of a vibration wave form;

DETAILED DESCRIPTION OF THE PREFERRED EMBODIMENTS

Now, referring to the accompanying drawings, embodiments according to the present invention will be described in the following.

First, the theory of a defect detecting method and apparatus will be described. The defect detecting method and apparatus was invented according to the result of the following study conducted by the inventor.

Figure 1A:
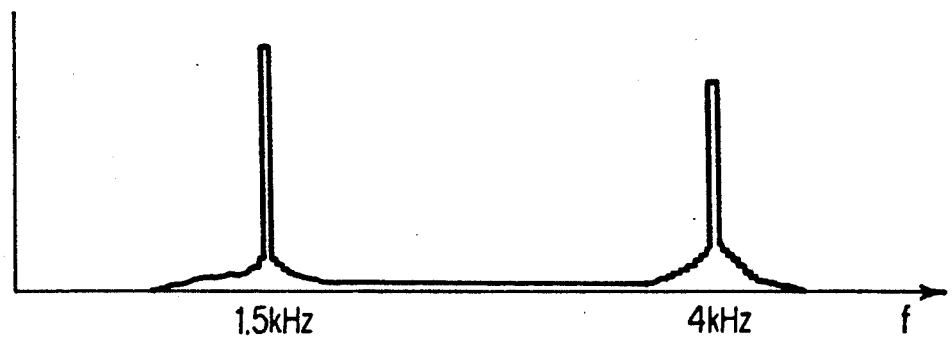
FIG. 1A is a spectrum of the characteristics vibration with a hollow cylinder which does not have a defect.

Now, as an example, suppose a hollow cylinder part made of a casting as an object to be measured. Vibrate the cylinder part by applying a shock. Pick up the vibration by means of a displacement meter or an vibration detecting sensor with a high directivity. At that time, when the spectrum of the characteristic vibration of the hollow cylinder which does not have a defect such as a crack, a void, or an dent is analyzed, as shown in FIG. 1A, a peak is observed in each of the spectrum orders (such as first order, second order, etc.). In this spectrum, frequencies where peaks take place are determined by the shape, material, and size of the object to be measured.

Figure 2:
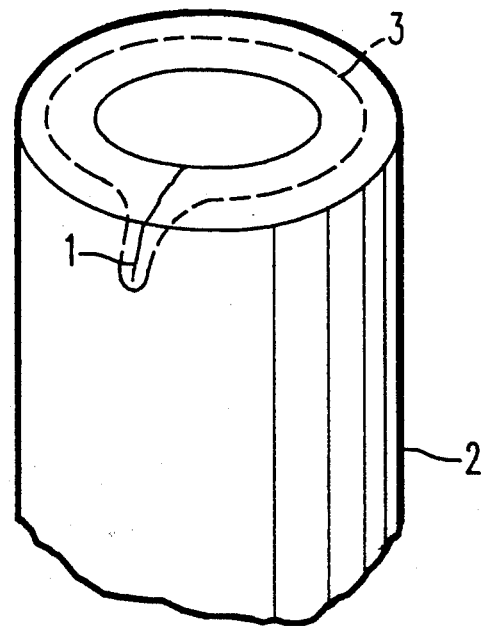
FIG. 2 is a schematic describing the theory of detection according to the present invention.

On the other hand, when the cylinder of the object to be measured has a crack which pierces through the wall thereof, two peaks which are separated are observed in each odd order of the spectrum. As shown in FIG. 2, since a crack 1 is present, a vibrating wave which propagates from the cylindrical wall of the cylinder 2 cannot passes through the crack 1, but detours the way shown by a dot line 3, thereby lengthen a path of propagation of the vibration. As a result, a vibration spectrum due to the crack takes place on the lower frequency side than the spectrum of the basic characteristic vibration of the cylinder part.

Figure 1B:
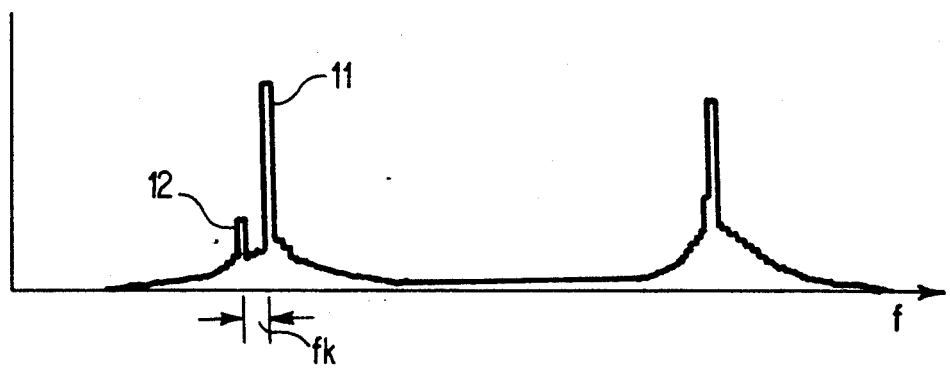
FIG. 1B is a spectrum of the characteristic vibration of a hollow cylinder containing a crack.

In other words, when only a crack is present in the cylinder part, as shown in FIG. 1B, a peak 12 of the vibration spectrum due to the crack separately takes place below a peak 11 of the first order spectrum of the basic characteristic vibration spectrum. The sum of the energy of both the spectrums is equal to the energy of the first order spectrum shown in FIG. 1A where the crack is absent. In the second order spectrum of FIG. 1B, there is only one peak.

In this case, the size (length) of the crack is proportional to a frequency difference fK between the peaks 11 and 12 of the spectrum. The size of the crack represents the volume of the crack portion. When the object to be measured is a cylinder, the thickness is constant and the width of the crack can be almost ignored. Thus, the size of the crack represents the length of the crack. In this case of the cylinder part, it was verified that the frequency difference fK of 5 Hz represents a 4 mm long crack.

When the crack is very small, the Q value of each odd order spectrum ($=(f1-f2)/f0$) (see FIG. 3) increases and the width becomes large. It is supposed that this situation is observed since the spectrum of the basic characteristic vibration and the spectrum of the vibration due to the crack are not separated, but connected because of the frequency resolution of the computation unit.

Thus, by detecting the magnitude of the Q value of an odd order spectrum, for example, the first order spectrum, it can be determined whether the crack is present or absent.

Figure 1C:
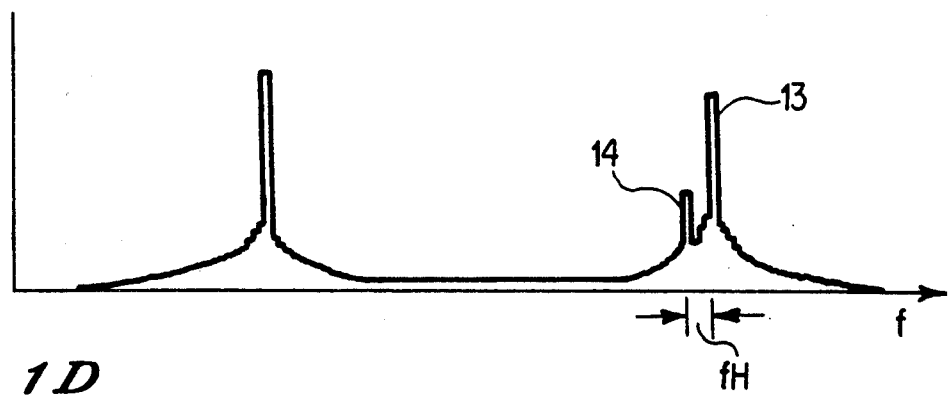
FIG. 1C is a spectrum of the characteristic vibration of a hollow cylinder containing a non-through defect such as a void or a dent.

On the other hand, when the cylinder part of the object to be measured has a non-through defect, which does not pierce through the wall, for example, a casting cavity or a dent, unless an another crack which is a through defect is present, an odd order spectrum, such as the first order spectrum or the third order spectrum, is not separated as shown in FIG. 1C. Thus, only by observing the odd order spectrums, the non-through defect such as the casing cavity cannot be detected. The vibration which takes place as the first order spectrum propagates the circumference of the cylinder part. Thus, for a defect such as a dent, the vibration does not pierce through the wall of the cylinder and does not need the detour. Consequently, the spectrum is not separated into two peaks.

However, when focusing on an even order spectrum, for example, the second order spectrum, since the portion of the dent or the like has a detour in the direction of the thickness, the spectrum which is separated into two peaks can be observed.

In other words, as shown in FIG. 1C, when only a non-through defect such as a void or a dent is present in an object to be measured, the second order spectrum is separated into two peaks, which are a peak 13 of the spectrum of the basic characteristic vibration and a peak 14 of the spectrum of the vibration due to the non-through defect. The sum of the energy (amplitude) of both the spectrums is equal to the energy where the non-through defect is absent. In addition, for the same reason as described above, the spectrum of the vibration due to the non-through defect takes place at a lower frequency than the second order spectrum of the basic characteristic vibration.

In this case, a frequency difference fH between the peak 13 and the peak 14 of both the spectrums is proportional to the size of the non-through defect.

When the non-through defect such as a casting cavity or a dent is very small, like the case of the crack, although the spectrum of the vibration due to the non-through defect disappears in the spectrum of the second order basic characteristic vibration, the Q value becomes large. Thus, by determining the magnitude of the Q value, it is possible to detect a very small casting cavity or dent.

Figure 1D:
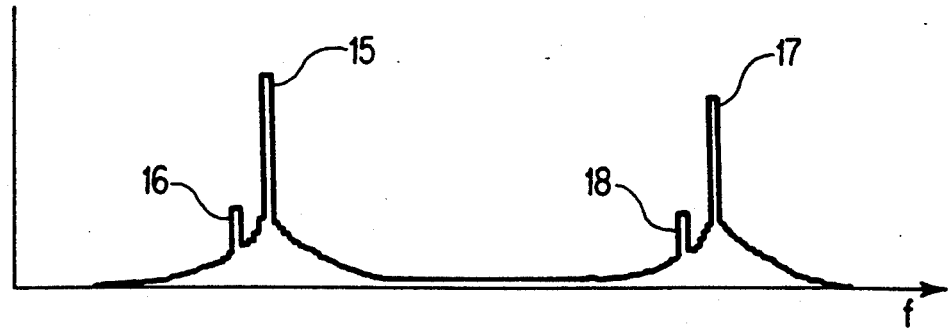
FIG. 1D is a spectrum of the characteristic vibration of a hollow cylinder containing both a crack and a void or dent.

Then, when both a through defect such as a crack and a non-through defect such as a casting cavity or a dent are present at the same time (the case that a crack is present along with a dent often takes place), as shown in FIG. 1D, each of the first order spectrum and the second order spectrum of the basic characteristic vibration has two peaks. In the first order spectrum, a peak 15 is the spectrum of the basic characteristic vibration, and a peak 16 below the peak 15 is the spectrum of the vibration due to a through defect such as a crack. In the secondary spectrum, a peak 17 is the spectrum of the basic characteristic vibration, and a peak 18 below the peak 17 is the spectrum of the vibration due to a non-through defect such as a dent. However, the size of the non-through defect is obtained by subtracting the frequency difference fK of the two peak positions of the first order spectrum from the frequency difference fH at the two peak positions of the second order spectrum because the spectrum due to the non-through defect is affected by a crack, which is a through defect.

The vibration to be considered is the characteristic vibration intrinsic to the shape of the object to be measured. However, when the object to be measured is forcedly vibrated, a longitudinal wave initially takes place like the forced vibration and an earthquake wave. The longitudinal wave is mixed with the characteristic vibration. Thus, when the crack or the dent is remarkably large, even if other waves are mixed with the characteristic vibration, the defect may be detected in the aforementioned manner. However, usually, unless waves other than the characteristic vibration are satisfactorily removed, it is difficult to detect the defect.

The present invention solves such a problem in the following manner.

When the object to be measured is vibrated, the sine wave method or impulse shocking method can be used. When the sine wave method is used, the object to be measured is vibrated under a constant condition, at a particular moment the vibration being stopped. After a small time period elapsed from that, the measurement of the vibration is started.

On the other hand, when the impulse method is used, a shock is applied to an object to be measured so as to vibrate it. After a small time period elapsed, the measurement is started.

In these cases, the time period after the vibration is stopped or that after the shock is applied until the measurement is started can be determined by using the following theory. The velocity c of a sound wave which propagates in the object to be measured depends on its Young's modulus E (elastic coefficient) and its density, where the following equation is satisfied.

$$c = \sqrt{E/\rho}$$

For example, when the impulse shock method is used, if a casting cylinder is the object to be measured, the velocity of the longitudinal wave is 4560 m/s, the velocity of the transversal wave being 1/1.8 times that of the longitudinal wave, namely, approx. 2780 m/s. Thus, the wave form in time series of the vibration being picked up after the shock is applied is shown in FIG. 4A. In this wave form, the fast portion of the longitudinal wave lasts for approx. 26 $\mu$sec. After that, the transversal wave is detected. After the peak value of the vibration of the transversal wave, the vibration is exponentially damped and then stopped.

As shown by the wave form of FIG. 4A, the vibration of the object to be measured just after it is vibrated is the same as that of an earthquake wave. Thus, the fast longitudinal wave and the slow wave are mixed. In addition, the resultant vibration includes the forced vibration. In other words, the characteristic vibration wave form intrinsic to the shape of the object to be measured does not take place. It is understood that the characteristic vibration wave form intrinsic to the shape is observed just before the vibration is stopped like the "precession" of a top.

In more detail FIG. 4A shows detection of the transverse wave beginning at time A after application of a shock, a peak value of the transverse wave occurring at time B after application of the shock, decay of the picked up vibration occurring after time B and notably at time C and at a further time D. FIG. 4A shows time along the x axis.

FIGS. 4B and 4C show emphasizing windows to be applied to the vibration wave form such as the one shown in FIG. 4A for excluding from subsequent analysis, all wave form signal outside of the time range between times C and D.

Thus, in this case, the vibration since the peak value of the transversal wave is completed until the damping of the vibration is started, is picked up. To do that, a rectangular wave form window W1 is set as shown in FIG. 4B. In this example, with the window W1, the vibrating wave is picked up.

In this example, the window W1 goes up after the shock is applied and 20 msec elapsed, the width of the window being 200 msec.

As described above, even if the portion of the characteristic vibration wave form intrinsic to the shape of the object to be measured is picked up, a very small crack, dent, and casting cavity tend to disappear in the spectrum of the basic characteristic vibration. In this case, they should be detected by using the Q value.

Figure 3:
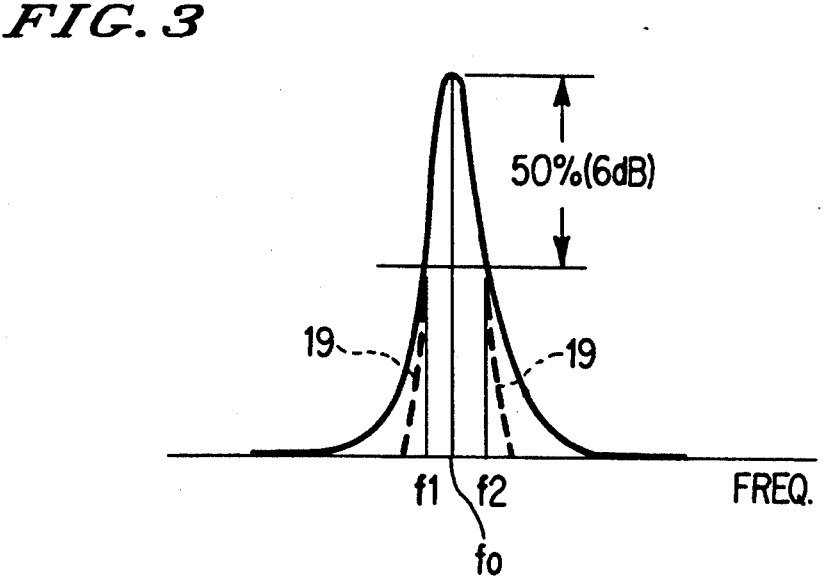
FIG. 3 is a schematic describing a Q value.

In view of this, it is considered that the length of the "foot" of the spectrum wave form of the basic characteristic vibration is satisfactorily decreased so as to easily determine a crack and a casting cavity. For that reason, the spectrum wave form shown in FIG. 3 is compensated so that it is sharply damped from 50% of the peak (the Q value is not changed) as shown by a dot line 19 of the figure. Consequently, since the "foot" of the spectrum wave form becomes narrow, even if a defect such as a crack or a dent is very small, the spectrum of the basic characteristic of the vibration and the spectrum of the vibration due to the defect can be separately detected without using the Q value of the spectrum of the defect.

To emphasize the spectrums as described above, it is necessary to further apply an emphasizing window W2 with a wave form represented with the following equation to the vibration wave form being picked up.

$$y = a \cos^2 (x\omega t) + b \cos^2 (x\omega t + \tau) + \ldots + k \cos^2 (x\omega t + n\tau) + C$$

where $\tau$ is a time delay, for example, $\lambda/4$ ($\lambda$ is a wave length). In this example, the relationship of $a=b=\ldots=k$ is satisfied. The emphasizing window W2 is a wave form as shown in FIG. 4C.

Figure 5A:
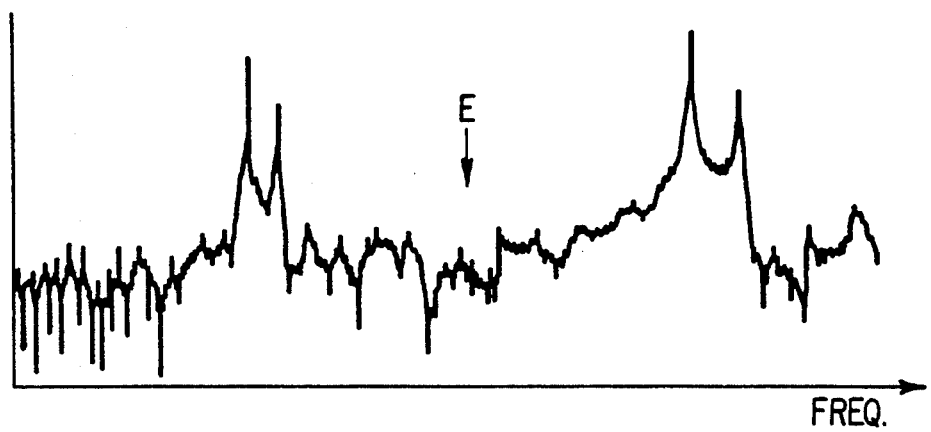
FIG. 5A shows a spectrum of the entire vibration of the object to be measured being picked up.
Figure 5B:
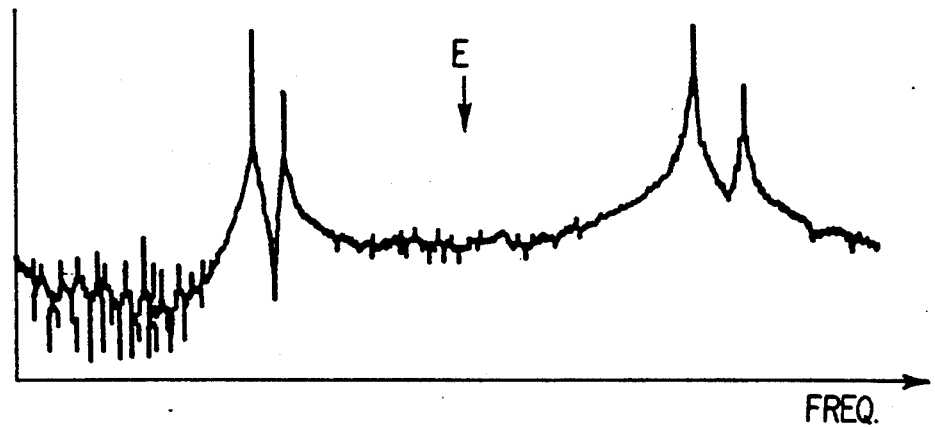
FIG. 5B shows a spectrum of a vibration waveform picked up by means of the characteristic vibration picking up window W1.
Figure 5C:
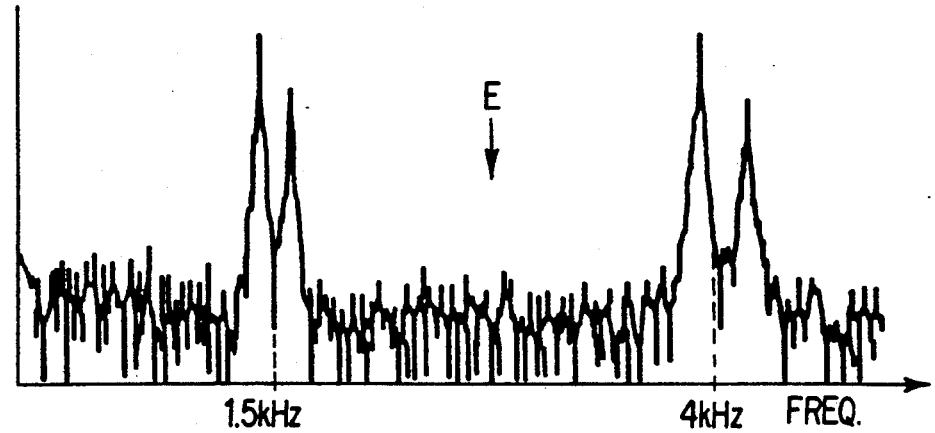
FIG. 5C shows a spectrum waveform in which the emphasizing window W2 is applied.

In FIGS. 5A–5C various portions of the spectra shown in FIG. 4A have been transformed to frequency domain. FIG. 5A corresponds to transformation of all of the time domain wave form of FIG. 4A. FIGS. 5B and 5C correspond to transformation of the spectra of FIG. 4A, after the emphasizing window of FIGS. 4B and 4C, respectively, has been applied to the spectra of FIG. 4A.

FIG. 5A shows a spectrum of the entire vibration of the object to be measured being picked up, where the characteristic vibration picking up window W1 and the emphasizing window W2 are not applied. FIG. 5B shows a spectrum of an vibration wave form picked up by means of the characteristic vibration picking up window W1, the wave form being picked up 20 msec after a shock of vibration is applied to the object to be measured, where the separation of the spectrum of the basic characteristic vibration and the spectrum of the vibration due to the defect can be observed. FIG. 5C shows a spectrum wave form in which the emphasizing window W2 is applied, where the separation of the spectrum of the basic characteristic vibration and the spectrum of the vibration due to a defect such as a crack or a dent can be much clearly observed.

FIGS. 5A, 5B, and 5C also show, in an exemplary fashion, a frequency E, between the frequency peaks associated with the first and second order vibrations of the object.

In the aforementioned method, the spectrum of the vibration is analyzed. In addition, it is possible to detect whether a defect such as a crack, a dent, or a void is present or absent by applying the windows W1 and W2 to the vibration being picked up and then by converting the result into a wave form in time series.

Figure 6:
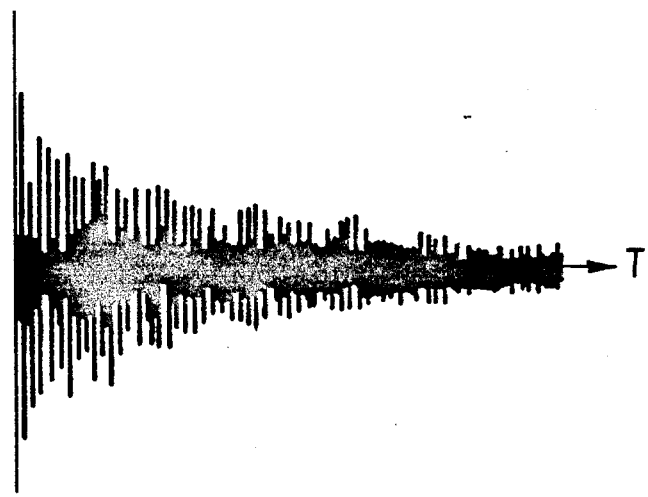
FIG. 6 is a waveform of vibration of an object without defects.
Figure 7:
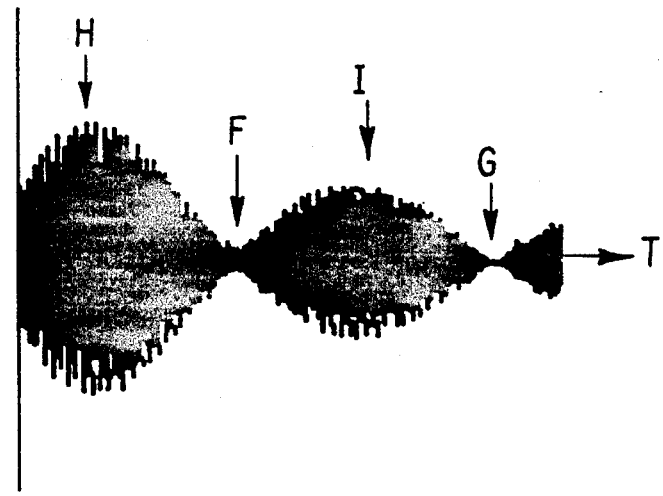
FIG. 7 is a waveform of a first order spectrum versus time.
Figure 8:
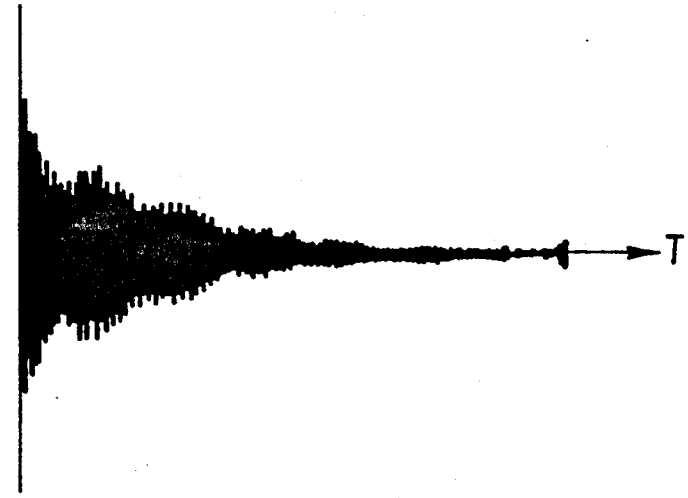
FIG. 8 is a waveform of a second order spectrum versus time.

In other words, in the case that no defect is present, when the windows W1 and window W2 are applied to a vibrating wave after 20 msec elapsed (see FIG. 6) and then converted into a wave form in time series, the crest becomes one envelope. FIG. 6 shows such a case where the frequency spectrum shown in either of FIGS. 5B or 5C, in which one of the windows has been applied, is then transformed back to time domain. However, the exponential decay envelope seen in FIG. 6 only occurs when no defects are present. When a defect is present and a vibration waveform has had an emphasizing window applied and then been transformed to frequency space, as shown in either FIGS. 5B or 5C, and then a portion of this spectrum is retransformed to time domain, the wave forms shown in FIGS. 7 and 8 result. The wave forms of FIGS. 7 and 8 correspond to time series of the first and second order spectrum, respectively. The wave forms of the time series shown in FIGS. 7 and 8 are arrived at by converting a portion of the frequency spectrums shown in FIGS. 5B or 5C, which correspond to one order of vibrations, into time domain to form a wave form in time series. As can be seen in FIGS. 5B and 5C the portion of the frequency spectrum containing the peaks corresponding to first order vibrations occur in a portion of the frequency spectrum below a frequency E. Peaks corresponding to second order vibrations occur in a portion of the frequency spectrum above frequency E.

As can be seen in FIGS. 7 and 8 the envelope of the resulting time series wave forms for a sample containing a defect contain oscillations. As seen in FIG. 7 the oscillations have crests H, I, and minima F, G as a function of time. The relative frequency of the crests, or equivalently the number of crests per unit time in the time series shown in FIGS. 7 and 8 is proportional to the size of defect in the object being tested.

On the other hand, when a defect such as a crack, dent, or void is present, as shown in FIGS. 7 and 8, a wave form with two or more crests takes place. FIG. 7 is a wave form in time series with respect to the first order spectrum. FIG. 8 is a wave form in time series with respect to the second order spectrum.

In this case, the number of crests which take place in the envelope is proportional to the size (length) of the defect.

Figure 9:
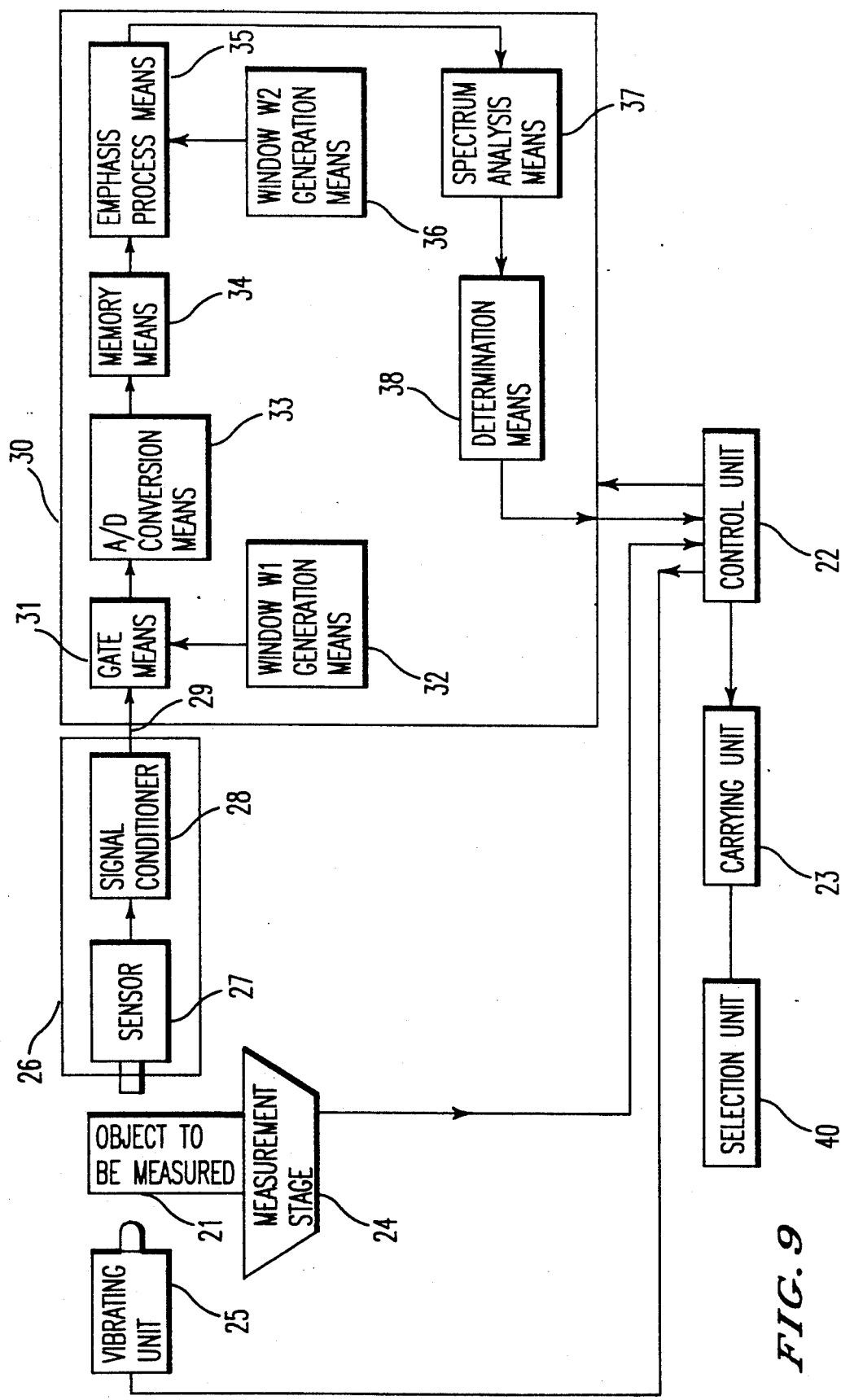
FIG. 9 is a schematic showing an embodiment of a defect detecting apparatus according to the present invention.

FIG. 9 is an embodiment of a defect detecting apparatus which was described above. This embodiment is an example of an apparatus for automatically inspecting all cylinder parts on a production line and for determining whether they are good parts or not good parts.

For example, the cylinder part as an object to be measured 21 is carried on a line by means of a carrying unit 23 which is controlled by a control unit 22 having a microcomputer, the cylinder part being placed on a measurement stage 24.

The measurement stage 24 is composed of a hard rubber, for example. When a sensor or the like disposed on the measurement stage 24 detects that the object to be measured 21 is placed on the measurement stage 24, the control unit 22 drives an vibrating unit 25 so as to vibrate the object to be measured 21. In this example, the vibrating unit 25 pendulously applies a shock to a position other than the center of gravity of the object to be measured 21 with a weight. The drive mechanism of the weight is structured with a cam mechanism so that after the shock is applied, the weight is immediately moved from the object to be measured.

The vibration of the object to be measured 21 is detected non-contactually by a sensor 27 of an output vibration receiving unit 26 and then converted into an electric signal The resultant signal is processed in a particular manner by a signal conditioner 28. The sensor 27 may be any substitute which can detect an vibration, for example, a displacement meter. It is preferable that the sensor 27 has a sharp directivity to prevent it from picking up noise vibrations in the vicinity thereof. The signal conditioner 28 amplifies the electric signal and removes high and low range components (trends), which are not necessary. In the case of the cast iron cylinder part, the first order spectrum and the second order spectrum of the basic characteristic vibration are present for example at 1.5 kHz and at approx. 4 kHz, which is approx. 2.8 times the former, respectively.

The electric signal from the output vibration receiving unit 26 is sent to a computation process and determination unit 30 through a transmission line 29. For example, the computation process and determination unit 30 is provided with a microcomputer, the microcomputer executing a computation operation and a determination operation (will be described later) by means of software. The operations in the computation process and determination unit 30 are illustrated as functional blocks of the figure. The electric signal being input is sent to a gate means 31. A window W1 generation means 32 generates a rectangular wave window W1 which goes high for 20 msec to 200 msec after the aforementioned shock is applied in accordance with the vibration start information which is sent from the control unit 22. The window W1 is sent to the gate means 31 so as to pick up the characteristic vibration component according to the shape of the object to be measured. The characteristic vibration component is converted into digital data by an A/D conversion means 33 and then written to a memory means 34. The digital data is read from the memory means 34. A wave form emphasizing process means 35 applies to the digital data an emphasizing window W2 generated by a window W2 generation means 36. The resultant data is sent to a spectrum analysis means 37. The spectrum analysis means 37 analyzes the spectrum of the resultant data. Like the window W1, the emphasizing window W2 is generated in accordance with the vibration start information from the control unit 22.

Figure 10:
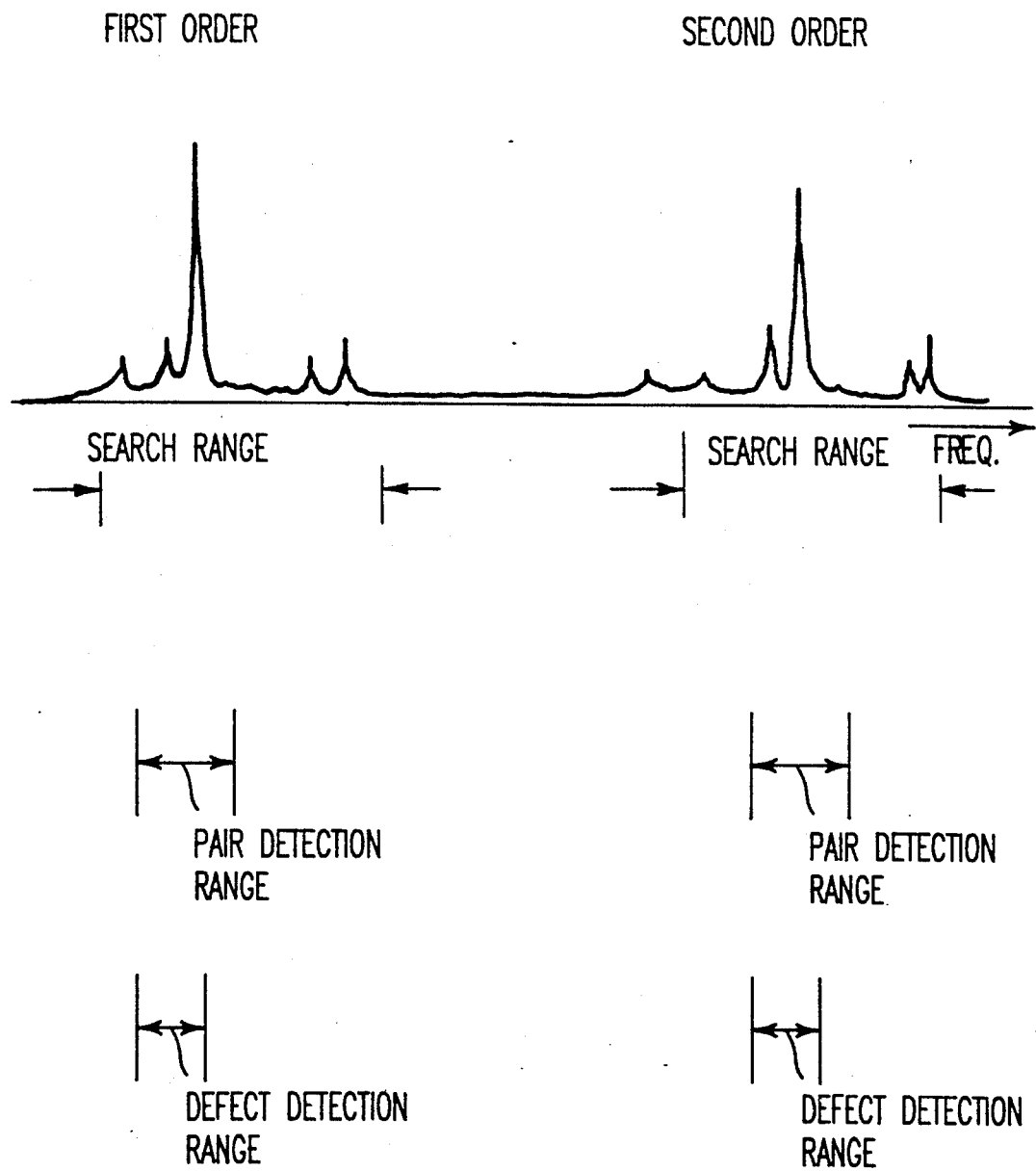
FIG. 10 is a schematic describing the operation of the embodiment shown in FIG. 9.

As shown in FIG. 10, a determination means 38 obtains large peak values, for example, five large peak values from the spectrum wave form from the spectrum analysis means 37 in a predetermined first order spectrum frequency range d1 and a predetermined second order spectrum frequency range d2, respectively and stores the frequencies and the peak values. Then, for the first order spectrum and the second order spectrum, frequency ranges where the spectrum of the basic characteristic vibration and the spectrum of the vibration due to a defect such as a crack, casting cavity, or dent are paired, respectively, namely d3 and d4 are predetermined, where the relationship of d3, d4<d1, d2 is satisfied. In the frequency ranges d3 and d4, it is determined whether the pair is present or absent in the five large peak values. When the pair is detected in the first order spectrum, the higher frequency of the lower frequency pair is determined as the position of the first order spectrum of the basic characteristic vibration. In accordance with this frequency position, it is determined whether or not another peak (or a pair of peaks) other than the spectrum of the basic characteristic spectrum vibration is present in a predetermined frequency range d5, which is narrower than the aforementioned frequency range d3. When the peak is present, it is determined that the object to be measured has a crack.

Likewise, when a pair is detected in the second order spectrum, the higher frequency of the low frequency pair is determined as the position of the second order spectrum of the basic characteristic vibration. In accordance with the frequency position, it is determined whether another peak other than the spectrum of the basic characteristic vibration is present or absent in a predetermined frequency range d6, which is narrower than the aforementioned frequency range d4. When the peak is present, it is determined that the object to be measured has a casting cavity or a dent.

In the aforementioned manner, the presence or absence of a defect is detected with respect to the first order spectrum and the second order spectrum.

Figure 11:
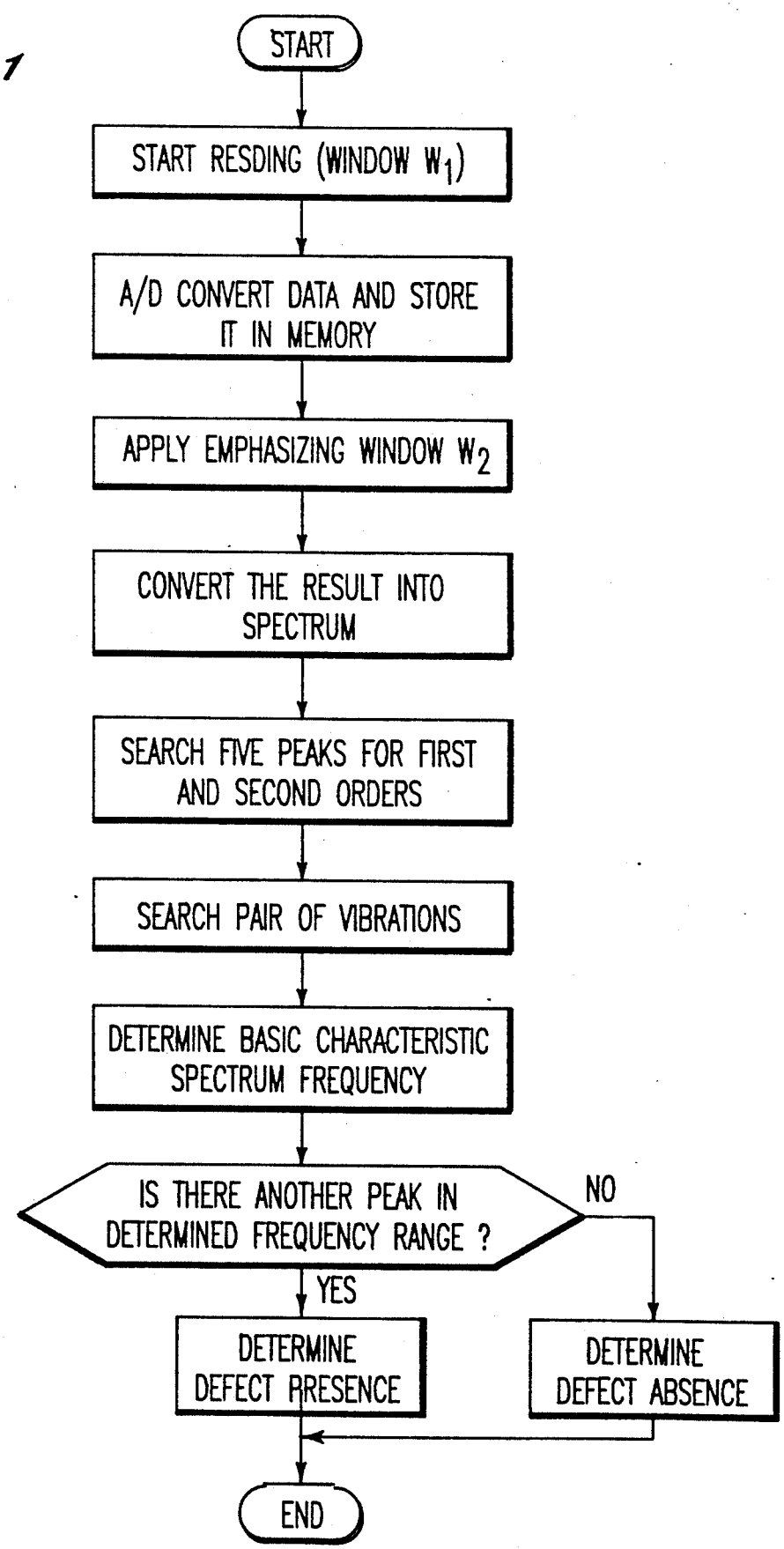
FIG. 11 is a flow chart of the embodiment shown in FIG. 9.

FIG. 11 shows a flow chart showing the operation of the computation process determination unit 30.

When it is determined that the part has a defect, a selection unit 40 removes it from the line as a defective part. On the other hand, when it is determined that the part has no defect, the part is sent to the next process. Thus, for all the parts, it is determined whether or not they have a defect.

Actually, before the finishing operation of the cylinder part is conducted, it is preferable to determine whether or not the cylinder part has a crack. After the finishing operation is conducted, it is preferable to determine whether or not the cylinder part has a casting cavity or a dent.

In other words, since a casting cavity or a dent may be removed in the finishing operation, it may not be determined that the cylinder part has a defect. In addition, when the finishing operation is conducted for the cylinder part with a crack, the part may be dangerously broken and the byte of the lathe may be damaged.

Thus, on the line, for the cylinder part which has not been finished, it is determined whether or not it has a crack by focusing on the first order spectrum by using the aforementioned apparatus. The part with a crack is removed as a defective part.

Then, for the cylinder part which has been finished, it is determined whether or not it has a casting cavity or a dent by focusing on the second order spectrum by using the same apparatus. When it is determined that the part has a casting cavity or a dent in this inspection, it is removed as a defective part.

In the apparatus shown in FIG. 9, the computation process and determination unit analyzes the first order spectrum and the second order spectrum and then determines whether the part has a defect by using the theory where each spectrum is separated when the part has a defect. However, as was described above, even if it is determined that each of the first order spectrum and the second order spectrum is not separated when they are analyzed, if the magnitude of the Q value being measured is larger than that in the case that the part has no defect such as a crack, it can be determined that the part has the defect so as to improve the accuracy of the measurement.

In addition, besides the spectrum analysis, it is possible to store the wave form data of the vibration, to convert it into time series, to detect its envelope, and then to count the number of crests so as to detect a crack in the part.

In the aforementioned embodiment, the cylinder part as the object to be measured was described. However, any shape can be considered as the object to be measured. For example, the object to be measured may be a cube or another polyhedron. In addition, any material is also considerable.

Moreover, besides the impulse shock method, various vibrating methods are also considerable, for example, it is possible to deformatively vibrate the part by fixing its end.

What is claimed is:

1. A defect detecting method for detecting defects in an object, comprising the steps of:

applying a vibration to said object until a first predetermined time;
recording a vibration wave form from said object after said first predetermined time;
determining a first time after a peak value of said vibration waveform and a second time after said first time,
applying to said vibration wave form, an emphasizing window which emphasizes said vibration wave form from between said first time and said second time, thereby defining an emphasized vibration wave form;
transforming the emphasized vibration wave form to frequency domain to form a transformed vibration spectrum, wherein said transformed vibration spectrum has all peaks corresponding to each vibrational order of said object in a limited frequency range;
retransforming a limited frequency range containing all peaks corresponding to a selected vibrational order to time domain, thereby forming a wave form in time series of said selected vibrational order;
determining an envelope of the wave form in times series of said selected order, wherein oscillations in said envelope indicate defects in said object.

2. A method according to claim 1, wherein:
a frequency of oscillation in the envelope of the wave form in time series of said selected vibrational order corresponds to a size of defects in said object.

3. A method according to claim 1, further comprising:
signal processing of said transformed vibration spectrum which sharpens peaks therein.

4. A method according to claim 3, wherein:
said signal processing step does not change Q values of said peaks.

5. A defect detecting device for detecting defects in an object, comprising:
first applying means for applying a vibration to said object until a first predetermined time;
recording means for recording a vibration wave form from said object after said first predetermined time;
first determining means for determining a first time after a peak value of said vibration waveform and a second time after said first time,
second applying means for applying to said vibration wave form, an emphasizing window which emphasizes said vibration wave form from between said first time and said second time, thereby defining an emphasized vibration wave form;
transforming means for transforming the emphasized vibration wave form to frequency domain to form a transformed vibration spectrum, wherein said transformed vibration spectrum has all peaks corresponding to each vibrational order of said object in a limited frequency range;
retransforming means for retransforming a limited frequency range containing all peaks corresponding to a selected vibrational order to time domain, thereby forming a wave form in time series of said selected vibrational order;
second determining means for determining an envelope of the wave form in times series of said selected vibrational order, wherein oscillations in said envelope indicate defects in said object.

6. An apparatus according to claim 5, wherein:
a frequency of oscillation in the envelope of the wave form in time series of said selected vibrational order corresponds to a size of defects in said object.

7. An apparatus according to claim 5, further comprising:
signal processing means for signal processing of said transformed vibration spectrum which sharpens peaks therein.

8. An apparatus according to claim 9, wherein:
said signal processing means does not change the Q values of said peaks.

9. An apparatus according to claim 5, wherein:
said recording means includes one of a microphone and a displacement meter.

* * * * *